(12) United States Patent
Bernardin et al.

(10) Patent No.: US 10,131,614 B2
(45) Date of Patent: Nov. 20, 2018

(54) ESTERIFICATION UNIT FOR PRODUCING CRUDE METHYL METHACRYLATE, ESTERIFICATION PROCESS USING SAID UNIT AND PLANT COMPRISING SAID UNIT

(71) Applicant: Arkema France, Colombes (FR)

(72) Inventors: Yves Bernardin, Thionville (FR); Romain Billon, Carrieres sur Seine (FR); Xavier Marcarian, Billere (FR); Florent Vallet, Ecully (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/028,745

(22) PCT Filed: Oct. 17, 2014

(86) PCT No.: PCT/EP2014/072366
§ 371 (c)(1),
(2) Date: Apr. 12, 2016

(87) PCT Pub. No.: WO2015/055842
PCT Pub. Date: Apr. 23, 2015

(65) Prior Publication Data
US 2016/0257639 A1 Sep. 8, 2016

(30) Foreign Application Priority Data
Oct. 18, 2013 (FR) ..................... 13 60181

(51) Int. Cl.
*B01J 10/00* (2006.01)
*B01J 19/24* (2006.01)
(Continued)

(52) U.S. Cl.
CPC ............ *C07C 67/20* (2013.01); *B01J 4/002* (2013.01); *B01J 10/00* (2013.01); *B01J 19/1862* (2013.01); *B01J 19/245* (2013.01); *B01J 19/2445* (2013.01); *B01J 19/2465* (2013.01); *B01J 2219/0004* (2013.01)

(58) Field of Classification Search
CPC ..................................................... C07C 67/20
See application file for complete search history.

(56) References Cited

U.S. PATENT DOCUMENTS 3,996,950 A   12/1976   Mier
4,795,824 A * 1/1989   Kippax ................ C07C 67/08
                                                        203/14

(Continued)

*Primary Examiner* — Jennifer A Leung
(74) *Attorney, Agent, or Firm* — Thomas F. Roland (57) ABSTRACT

The invention relates to an esterification unit (150) and esterification process for producing crude methyl methacrylate (MMA) from methacrylamide (MAM), which enable particularly to improve the yield, meaning that the organics spent acids are low; and at the same time, providing crude MMA with rather good quality, meaning that MMA concentration in crude MMA is rather high and preferably from 50 wt % to 80 wt %. According to the invention, the esterification unit comprises esterification reactors (1, . . . , 5 (or 6) set up in a serial way so that there is a counter current flow between gaseous phase and liquid phase, the liquid phase flowing from first reactor (1) of the series to last reactor (5 (or 6)), and the gaseous phase flowing from reactor to first reactor (1).

18 Claims, 4 Drawing Sheets

(51) Int. Cl.
*C07C 67/20* (2006.01)
*B01J 19/18* (2006.01)
*B01J 4/00* (2006.01)

(56) References Cited

U.S. PATENT DOCUMENTS

| | | |
|---|---|---|
| 5,360,926 A | 11/1994 | Kouno et al. |
| 6,310,236 B1 | 10/2001 | Nakamura et al. |
| 2003/0208093 A1* | 11/2003 | Carlson, Jr. ............. C07C 51/06 562/598 |
| 2010/0029881 A1 | 2/2010 | Gropp et al. |
| 2014/0154758 A1 | 6/2014 | Dubois et al. |

* cited by examiner

ESTERIFICATION UNIT FOR PRODUCING CRUDE METHYL METHACRYLATE, ESTERIFICATION PROCESS USING SAID UNIT AND PLANT COMPRISING SAID UNIT

This application claims benefit, under U.S.C. § 119 or § 365 of PCT Application Number PCT/EP2014/072366, filed Oct. 17, 2014, and French Patent Application Number FR13.60181, filed Oct. 18, 2013, these documents being incorporated herein by reference.

FIELD OF THE INVENTION

The present invention relates to a continuous industrial process for the production of methyl methacrylate (MMA). It relates more particularly to a step of such industrial process and particularly to the step of esterification. The present invention relates more precisely to an improvement esterification unit for producing crude methyl methacrylate (MMA) from methacrylamide also called "MAM" (or "MACRYDE").

In general terms, methyl methacrylate is usually produced by the mean of acetone cyanohydrin process. Cyanhydric acid is first synthetised and then it is reacted with acetone to form acetone cyanohydrin. Finally acetone cyanohydrin is mixed with sulphuric acid to form methacrylamide. This amide is reacted with methanol to form methyl methacrylate. The main by-product of this process is spent acid outlet of esterification. The crude methyl methacrylate is recovered from esterification unit.

The invention relates more particularly to an improved unit for producing an optimized esterification reaction of methacrylamide with at least a reactant to form methyl methacrylate. The invention also concerned an esterification process using said unit and a plant to produce continuously methyl methacrylate (MMA) comprising said esterification unit.

STATE OF THE ART

A number of commercial processes are used to prepare monomer selected from methacrylic acid MAA and/or methyl methacrylate MMA. One of these processes consists in preparing such monomer from acetone cyanohydrin (ACH). Such a process is for example described in US patent application US2010/0069662. In this process, acetone cyanohydrin ACH is hydrolysed by sulphuric acid to produce a hydrolysis mixture of α-hydroxyisobutyramide (also called "HIBAM"), its sulfate ester, α-sulfatoisobutyramide also called "SIBAM", 2-methacrylamide MAM and methacrylic acid MAA. The hydrolysis mixture thus produced is then thermally converted, into a heated thermal conversion reactor, to a mixture mainly comprising 2-methacrylamide MAM and a small amount of MAA.

The acetone cyanohydrin ACH is subjected to an amidification for producing 2-methacrylamide (also called "MACRYDE").

MAM (MACRYDE) can be used to produce MMA by reaction of esterification with methanol, or it can be used to produce MAA by reaction of hydrolysis with water.

Methyl methacrylate MMA is mostly used to produce polymer such as polymethyl methacrylate (also called "PMMA") which has multiple applications like for example automotive, transport, aerospace, photovoltaic, informatics, telecommunications, wind energy, or building construction. MMA can also be used to produce other methacrylates by mean of trans-esterification.

The esterification step follows amidification step and the amidification section provides methacrylamide (MAM) in excess of sulphuric acid to the esterification unit.

The document US patent application 2010/029881 discloses a method for preparing alkyl methacrylate, comprising as steps of providing an acetone cyanohydrin; contacting the acetone cyanohydrin with an inorganic acid to obtain a methacrylamide; contacting the methacrylamide with an alcohol in the presence of an inorganic acid in a reactor to obtain an alkyl methacrylate. In that document the step of esterification is obtained by an esterification unit with at least one tank or preferably two tanks. The document disclosed preferred embodiment with two tanks. The first tank comprises input in the upper region for water and organics solvent, amide and alcohol and an input in the lower lever region of the tank for alcohol. For that a solvent line which conducts water and organics solvent and an amide line connected to an amidification section open into the tank.

The first tank is connected to a further tank via an ester vapour line and to the alcohol line both from the bottom and from the top. This further tank too is connected to the alcohol line both from the bottom and from the top. The ester vapour line is connected to the upper region of the second tank and opens into the bottom of a column. In addition, a line for dilute sulphuric acid is present in the upper region of this second tank. Such an esterification implementation is not quite satisfactory because of the yield of the reaction and because of the quality of the crude MMA produced.

The document EP 0945423 discloses a process for preparing alpha-hydroxycarboxylate. The process uses a unit comprising several reactors in serial way. However the ester is leaves the reactor by liquid conduits at the bottom.

The document EP 0594008 discloses a process for producing methyl methacrylate. The process uses an ion exchange resin as heterogeneous catalyst for the esterification of methacrylic acid with methanol for producing methyl methacrylate. Furthermore the described process uses stirrers as a mechanical agitating system.

The document U.S. Pat. No. 3,006,950 discloses a process of making methyl methacrylate. The described process is essentially a batch process, which does not comprise several reactors set up in a serial way. The process makes methyl methacrylate and methacrylic acid at the same time. The yield of the process according to the examples is between 90.5% and 91.5% with respect to acetone cyanhydrine and about 96.5% with respect to the amide. Furthermore the described process uses stirrers as a mechanical agitating system.

The MMA and MAA markets are extremely cost sensitive. A slight improvement in process yield can result in a significant market advantage.

TECHNICAL PROBLEM

Present invention aims to avoid at least one of the inconvenient of the state of the art.

Indeed, there is a continuing need to provide an equipment and process for producing crude methyl methacrylate (MMA) which enable particularly to improve the yield, more than 95% and preferably more than 97% meaning that the organics in spent acids are low. Spent acids are the main by-product of esterification step. At the same time, the equipment for producing crude MMA should produce crude MMA with rather good quality meaning that MMA concentration in crude MMA is rather high and preferably from 50 wt % to 80 wt %. In addition, it was another object of the present invention, to provide an equipment for producing methyl methacrylate from methacrylamide in a reliable way meaning, with no unplanned shut-down of esterification due to polymers fouling. As a result, the proposed esterification unit and process of esterification has an improved yield and is completely reliable.

More particularly, the invention aims to propose an esterification unit for producing crude methyl methacrylate comprising from methacrylamide (MAM), and at least methanol and water, comprising several reactors (1, . . . n, n+1, . . . , . . . N), each reactor having an upper part and a lower part, and wherein, the reactors are set up in a serial way so that there is a counter current flow between gaseous phase and liquid phase, the liquid phase flowing from first reactor (1) to last reactor (N or (N+1)), and the gaseous phase flowing from last reactor to first reactor,
 the first reactor of the series comprising:
  methacrylamide, methanol and water lateral inlets,
  at least a liquid phase outlet located at the bottom of the lower part,
 the last reactor comprising a lateral steam inlet located at the lower part,
 and each reactor also comprising:
  at least a gaseous phase outlet, at the top of the upper part,
  at least a gaseous phase inlet at the lower part, the reactors being connected in such a manner that the gaseous phase outlet of reactor n+1 is linked to the gaseous phase inlet of reactor n,
  at least a lateral liquid phase inlet located at the lower part, the reactors being connected in such a manner that the liquid phase outlet of reactor n is linked to the lateral liquid phase inlet of the reactor n+1
  at least another lateral liquid phase inlet located at the lower part, the liquid phase outlet of reactor n being linked to said another lateral liquid phase inlet of said reactor n.
According to other features of the invention:
 the second and/or third reactor of the series, comprises a liquid phase inlet at the lower part feed by methanol.
 each reactor comprises a gaseous phase distributor located inside the lower part of said reactor.
 the gaseous phase distributor comprises a pipe going horizontally from lateral wall of the reactor until the middle with at its end at least three nozzles in the liquid phase.
 said unit includes an additional reactor (N+1) comprising:
  at least a first and a second lateral liquid phase inlet located at the lower part,
  at least a gaseous phase outlet at the top of the upper part,
  at least a liquid phase outlet located at the bottom of the lower part,
  at least a lateral steam inlet located at the lower part,
  said additional reactor N+1, being connected in a parallel way to the last reactor N of the series in such a manner that said additional reactor N+1 is alternatively linked (via a valve) to the penultimate reactor N−1, its gaseous phase outlet being link to the lateral gaseous phase inlet of said penultimate reactor, and the liquid phase outlet of said penultimate reactor N−1 is linked to the first liquid phase inlet of the reactor N+1; the liquid phase outlet of said reactor N+1 being linked to its second lateral liquid phase inlet.
 said unit comprises a separation means to separate methacrylic acid from crude methyl methacrylate (MMA),
 said separation means being connected to the gaseous phase outlet of the first reactor.
 said separation means comprises:
  a first partial condenser (<100 wt %, 2 wt % to 50 wt %) for liquefying gaseous phase, having at least an inlet linked to the gaseous phase outlet of the first reactor with a temperature between 98° C. to 102° C., preferably 98° C. to 100° C., and at least an outlet providing liquid phase at a temperature between 80° C. and 84° C.,
  a drum device able to separate the obtained liquid phase from gaseous phase, separating acids from crude MMA, said drum device having an inlet connected to the outlet of the first partial condenser; and an acids outlet linked to the lateral liquid inlet of the first reactor and, having a gaseous phase crude MMA outlet,
  a total condenser for liquefying gaseous phase, preferably at least 99% of said crude MMA gaseous phase, said total condenser comprising a gaseous phase inlet linked to the gaseous phase outlet of the drum device, and an outlet for liquid phase of crude MMA,
  a drum linked to the outlet of the total condenser for recovering crude MMA, comprising a crude MMA outlet and a light components outlet,
  a trap condenser, linked to the light component outlet of the drum, for recovering said light components (methanol) and comprising an outlet vent event,
  and cooling device for cooling crude MMA, comprising an inlet linked to the crude MMA output of said recovery drum and comprising a crude MMA outlet with a concentration of MMA being of 50% to 80%, avoiding polymerisation.
 each reactor comprises two liquid phase outlet located at the bottom of the lower part, a first centrifugal pump being connected said an outlet and a second centrifugal pump being connected to the other said outlet, each centrifugal pumps having an outlet, said outlet being linked to the lateral liquid phase inlets located at the lower part of two successive reactors.
  each outlet is connected to a centrifugal pump (P) via a basket filters (F), and preferably with a basket filter for the 3rd pump to the last esterificator reactor pump (P).
 each reactor comprises at least a temperature control device (TA), a pressure control device (PA) and level control device (LC), said level control device regulates the flow of liquid outlet to get a constant liquid level inside each reactor,
  the lateral liquid phase flow is fed to reactors n and n+1, via control valve devices activated by level control device (LC).
 said unit comprises a steam control flow device able to regulate the steam flow according a predetermined flow rate (FC),
 partial condenser (70) and total condenser are cooled by water with flow controlled (CW),
 said unit comprises 3 to 8 esterification reactors n, more preferably 4 to 6 esterification reactors and more preferably 5 being set up in serial way and an additional esterification reactor being connected in a parallel way to the last reactor.
 the reactor vessels materials except for the last reactors, preferably include glass-lined materials; the last reactors (N, N+1) are zirconium, titanium, lead, nickel-based alloys such as nickel/molybdenum alloys sold as HASTELLOY B, B2 or B3, or iron/nickel alloys sold as INCOLOY, and tantalum alloys; steam distributor (90) and basket filters (F) are more preferably in iron/nickel alloy or in zirconium; and external gaseous pipes are glass lined pipes.

According to another aspect, the invention relates to a process for producing crude methyl methacrylate (MMA) from methacrylamide (MAM), and at least methanol and water with a series (1, . . . , n, n+1, . . . , N) of linked reactors, characterized in that it comprises an implementation of a counter current flow between gaseous phase and liquid phase, the liquid phase flowing from a first reactor (1) of the series to last reactor (N or (N+1)), and the gaseous phase flowing from last reactor to first reactor by:

Introducing liquids laterally into a lower part of the reactors, extracting gaseous phase from the top of the reactors and introducing gaseous phase of reactor n+1 into reactor n, extracting liquid phase from the bottom of the reactors and introducing liquid phase of reactor n into the reactor n+1, introducing steam laterally into the last reactor.

Preferably the mixing of the gaseous phase and liquid phase in said process is made with a gaseous phase distributor that distributes steam. More preferably the mixing of the gaseous phase and liquid phase in the series (1, . . . , n, n+1, . . . , N) of linked reactors in said process is made with a gaseous phase distributor that distributes steam in each rector.

Moreover, esterification process comprises advantageously optionally one of the following the steps of:

introducing gaseous phase flowing out from reactor n+1 with a distributor located inside reactor n for mixing said gaseous phase with liquid flow;

partially recycling liquid phase to the same reactor (n) to ensure mixing and, remaining part of liquid to the next reactor (n+1) after filtering small polymers from said liquid phase;

realize a first separation of acids from crude MMA at the outlet of the first reactor and recycling said acids by feeding a lateral liquid inlet of said the first reactor, and getting 60 wt % to 70% wt % crude MMA;

realize a second separation of acids from gaseous phase after first separation to get crude MMA containing mainly 50 wt % to 80 wt % of MMA, 10 wt % to 20 wt % of water and 10 wt % to 20 wt % of methanol and impurities;

controlling liquid level (L) of each reactor and maintaining said liquid level by regulating the flow introduction liquid phase with this controlling liquid level (L) to a constant level, said level being between preferably 25% to 75% of the total height of reactor;

controlling steam flow of the last reactor according to a predetermined flow rate, feeding laterally first reactor with methacrylamide, water and methanol, using 5 to 40% of methanol to fed the laterally second and/or third reactor,—feeding laterally last reactor with steam with a pressure of preferably 3 barg to 8 barg and having a molar ratio between steam and methacrylamide is between 1 and 2.5, a total water, liquid and vapour fed, being between 4 to 6.5 and, methanol being put in excess in comparison with methacrylamide from preferably 1, 1 to 2;

introducing an anti-fouling additive and/or polymerization inhibitors, to at least first reactor, said polymerization inhibitors including water soluble or alcohol soluble polymerization inhibitors and, introducing polymerization inhibitors at the first separation of acids from crude MMA.

The invention also relates to a plant to produce continuously methyl methacrylate (MMA) comprising an esterification unit as described above.

INTRODUCTION OF THE FIGURES

Other features and advantages of the invention will become apparent upon reading the following description given by way of illustrative and non-limiting examples, with reference to the accompanying Figures in which.

SPECIFICATION

The terms "top", "upper" or "above" and "down", "bottom", or "below" are used to define a part of reactor with respect to axis XX' of said reactor.

The term "reactor" is used to define esterification reactor.

Figure 1:
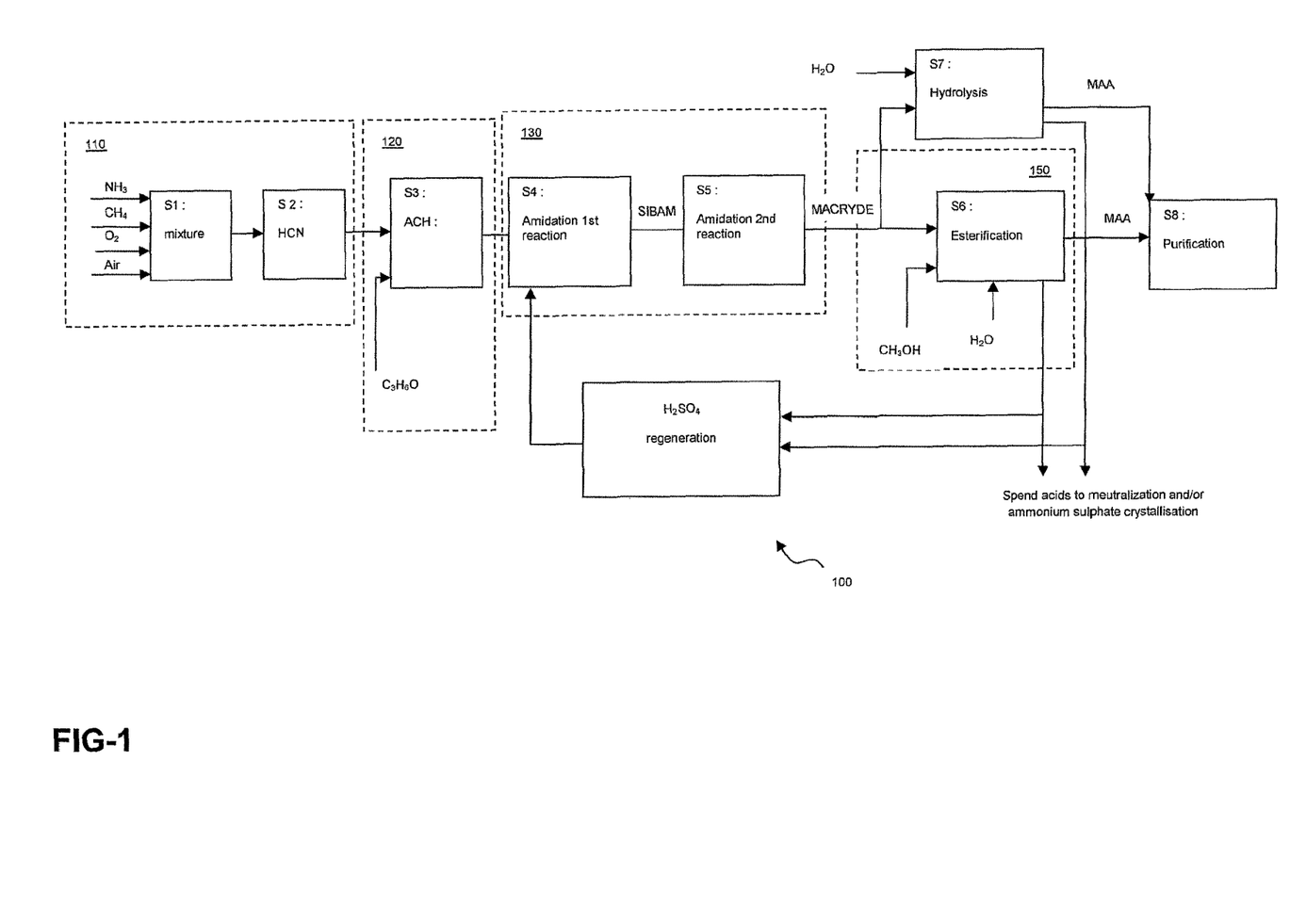
FIG. 1 represents a simplified schematic bloc diagram of a plant 100 for preparing methacrylic acid and/or methyl methacrylate.

The terms "upstream" and "downstream" are defined relative to the direction of a fluid flowing through the devices of a plant for the production of a final product such as methyl methacrylate (MMA) or methacrylic acid (MAA). Concerning the Synthesis of Monomer Selected from Methacrylic Acid and/or its Esters FIG. 1 shows a simplified schematic bloc diagram of a plant 100 for the production of methacrylic acid and/or its esters from acetone and hydrogen cyanide HCN prepared by the Andrussow process. The Andrussow process is for example described in the document U.S. Pat. No. 1,934,838.

Such monomers can be further used to produce for example polymethyl methacrylate (PMMA) that is a polymer widely used in a lot of applications like for example automotive, transport, aerospace, photovoltaic, informatics, telecommunications, wind energy, or building construction . . . .

Preparation of Hydrogen Cyanide HCN

First of all (steps S1 and S2) HCN is produced in a first unit 110, from a mixture of methane-containing gas, ammonia and air eventually enriched with oxygen. A mixture of reactant gases is prepared (step S1), and introduced (step S2) into an Andrussow type reactor comprising catalyst gauzes based on platinum/rhodium gauzes. Mixture of gases passes over the catalyst gauzes and reacts at a temperature comprised between 750° C. and 1250° C. and preferably between 1000° C. and 1200° C., to form HCN. The oxygen-enriched air enables to increase the productivity and to reduce the methane consumption. The HCN produced is quickly cooled and treated so as to avoid polymerization of HCN. For that, ammonia which has not reacted is absorbed by reaction with sulfuric acid, and the HCN is absorbed and stabilized in an absorption column, and then distilled in a distillation column to reach a purity of 99.5% wt.

Preparation of Acetone Cyanohydrin ACH

The thus synthesized HCN is then mixed with acetone ($C_3H_6O$), in a unit 120 designed for the production of acetone cyanohydrin ACH (step S3). The crude acetone cyanohydrin obtained is then purified by distillation.

Amidification of Acetone Cyanohydrin

A third unit 130 of the plant is provided for amidification of acetone cyanohydrin. Such amidification of ACH requires two steps S4 and S5 for producing 2-methacrylamide (also called "MACRYDE" in the following description).

First, in step S4, sulphuric acid ($H_2SO_4$) is added in excess in comparison with acetone cyanohydrin ACH. For example the molar ratio of $H_2SO_4$/ACH is comprised between 1.2 and 2, preferably between 1.25 and 1.8, and more preferably between 1.3 and 1.6.

This first reaction occurring is an hydrolysis reaction of ACH by sulphuric acid (H2SO4), which gives an intermediate salt, called the SIBAM (for α-sulfatoisobutyramide). This reaction is the following:

(CH3)2COHCN+H2SO4→(CH3)2COSO3HCONH2
Acetone cyanohydrin (ACH) α-sulfatoisobutyr-
amide (SIBAM)     (1)

This reaction is fast and exothermic. The temperature is comprised between 80° C. and 110° C. and the pressure is close to the atmospheric pressure.

The second reaction (step S5) is a slow and endothermic reaction. It occurs at atmospheric pressure and a temperature range between 110° C. and 165° C., preferably between 125° C. and 150° C. and more preferably between 130° C. and 145° C. This reaction is a cooking reaction which lasts between 3 and 16 minutes. This reaction is the following:

(CH3)2COSO3HCONH2→CH2C(CH3)CONH2+
H2SO4 α-sulfatoisobutyramide (SIBAM)
2-methacrylamide (MACRYDE)     (2)

During the synthesis reactions there are many other by-products. The main side reaction is described below.

The first hydrolysis reaction of ACH by a small quantity of water can create a significant quantity of HIBAM (α-hydroxyisobutyramide). Such a reaction is very fast. It is the following:

(CH3)2COHCN+H2O→(CH3)2COHCONH2 Acetone
cyanohydrin (ACH) α-hydroxyisobutyramide
(HIBAM)     (3)

In the second step S5, HIBAM can also create MACRYDE, but this reaction is very slow. So there is a large quantity of unconverted HIBAM at the end of amidification step S5. The reaction is the following:

(CH3)2COHCONH2→CH2C(CH3) CONH2+H2O
α-hydroxyisobutyramide (HIBAM) methacryl-
amide (MACRYDE)     (4)

The hydrolysis of HIBAM may create HIBA (α-hydroxyisobutyricacid)

(CH3)2COHCONH2, H2SO4+H2O→
(CH3)2COHCOOH+NH4HSO4 α-hydroxyisobu-
tyramide (HIBAM) α-hydroxyisobutyricacid
(HIBA)+ammoniumbisulfate     (5)

At the same time, a significant amount of methacrylic acid MAA is produced by the hydrolysis of SIBAM by water. This reaction is the following:

(CH3)2COSO3HCONH2+H2O→CH2C(CH3)COOH+
NH4HSO4 α-sulfatoisobutyramide (SIBAM)
methacrylic acid (MAA)+ammoniumbisulfate     (6)

The mixture of MACRYDE and MAA, also called mixture comprising 2-methacrylamide, obtained after amidification is then either hydrolyzed (step S7), by adding water to the MACRYDE mixture, or esterified (step S6), by adding methanol to the MACRYDE mixture.

Esterification

The components obtained after amidification, namely the methacrylamide and the methacrylic acid, are esterified by unit 150 of the plant, so as to obtain methyl methacrylate MMA. The esterification reaction (step S6) is made by mixing said components with methanol ($CH_3OH$).

The main reactions are these two below:

CH2C(CH3)CONH2, H2SO4+CH3OH→CH2C(CH3)
COOCH3+NH4HSO4 methacrylamide (MAC-
RYDE)+methanol methymethacrylate (MMA)+
ammoniumbisulfate     (7)

CH2C(CH3)COOH+CH3OH→CH2C(CH3)COOCH3+
H2O methacrylic acid (MAA)+methanol
methymethacrylate (MMA)     (8)

Hydrolysis

The components obtained after amidification can also be hydrolysed by mixing them with water (step S7). Such hydrolysis reaction allows to obtain methacrylic acid according to the following reaction:

CH2C(CH3)CONH2, H2SO4+H2O→CH2C(CH3)
COOH+NH4HSO4 methacrylamide (MAC-
RYDE) methacylic acid (MAA)+ammonium-
bisulfate     (9)

Purification of Crude MMA or MAA Obtained

Either the crude methyl methacrylate MMA obtained after esterification (S6) or the crude methacrylic acid MAA obtained after hydrolyse (S7) is then purified (step S8) by classical process known in the art, in order to remove residual compounds.

Used $H_2SO_4$ from esterification or hydrolysis maybe used to produce ammonium sulfate or maybe regenerated to produce sulfuric acid/oleum which can be recycled into the process.

Figure 2:
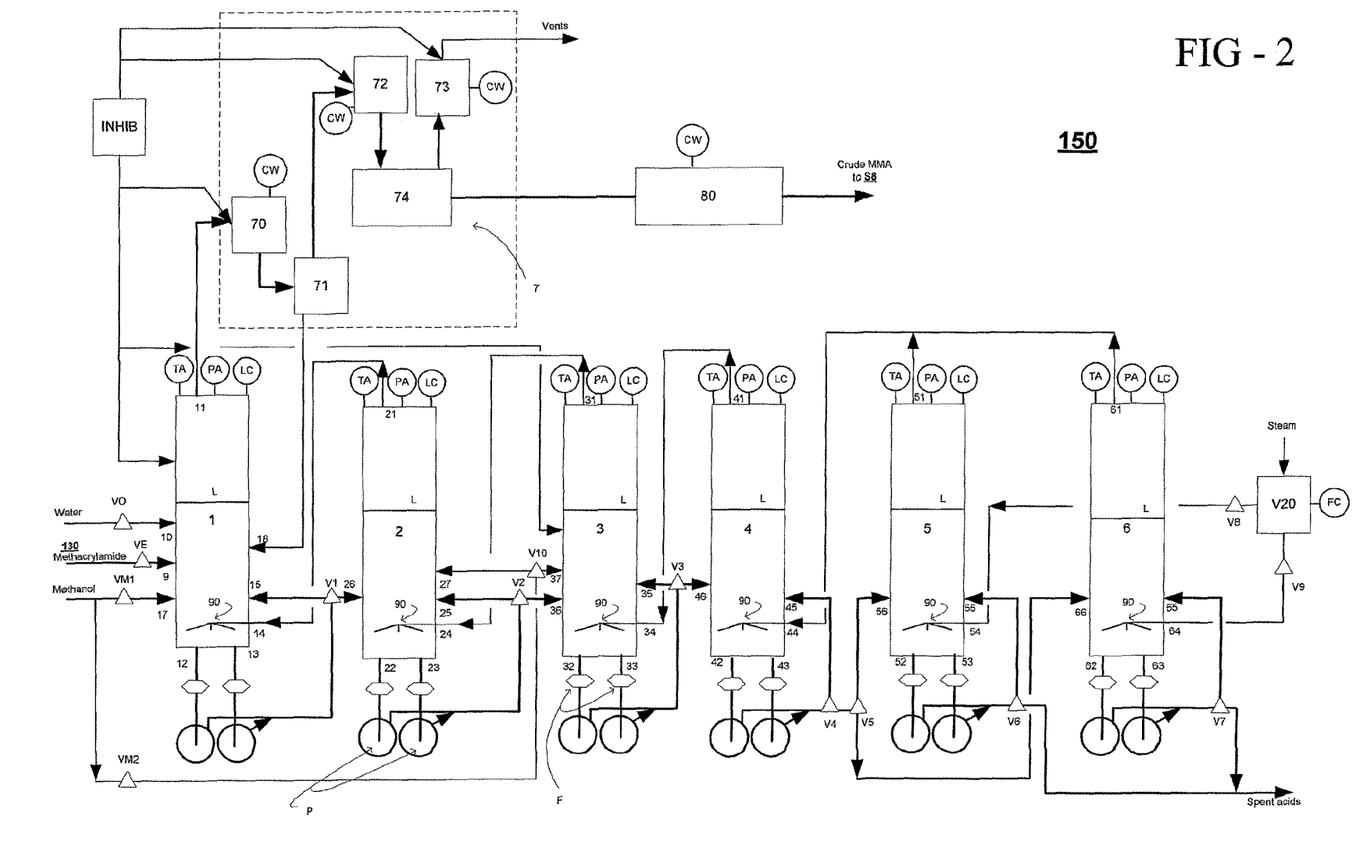
FIG. 2 represents a detailed view of the esterification unit 150 according to the invention.

Concerning the Esterification Unit 150,

FIG. 2 shows a view of the esterification unit 150 for producing crude methyl methacrylate MMA, according to the invention. The esterification unit 150 comprises 3 to 8 esterification reactors n and more preferably 4 to 6 esterification reactors. In the preferred embodiment represented on FIG. 2, the esterification unit comprises five esterification reactors 1, 2, 3, 4, 5. Each reactor n (1, 2, 3, 4, 5) comprises a lower part defined by the level L of liquid phase and an upper part above this level L containing gaseous phase. The liquid phase is extracted from the bottom of the reactors ie, from the bottom of the lower part, and the gaseous phase is extracted from the top of the reactors, ie, from the top of upper part.

Advantageously, the last reactor 5 is doubled with an additional (n+1) reactor 6, same as the others, set up in a parallel way with said last reactor 5 in such a manner that the reactor 6 operates alternately with the last reactor 5. Indeed last reactor is sensitive to fouling. Therefore, it must be cleaned up regularly. By adding a supplemental last reactor in the series, one reactor, for example reactor 5 is running whereas other one, reactor 6, is in cleaning operation or maintenance operation. The shift between both reactors is done thank to valve V5. By this way, reliability of esterification can be largely improved.

Moreover, according a feature of the invention, the reactors 1, 2, 3, 4 and 5 (or 6) are set up in a serial way so that there is a counter current flow between gaseous phase and liquid phase.

Indeed, the reactors n are linked in such a manner that the flow pattern is counter-current flow. That means, that liquid phase flows from first reactor 1 of the series to last reactor 5 (or 6) and, gaseous phase flows from last reactor 5 (or 6) to first reactor 1 of the series.

All liquid are introduced laterally on each reactor by lateral inlets identified 9, 10, 15, and 18 for reactor 1; 26, 25 for reactor 2; 36, 35 for reactor 3; 46, 45 for reactor 4; 56, 55 for reactor 5 and 66, 65 for reactor 6.

Liquid phases are extracted from the bottom of the reactors from outlets identified 12, 13 for reactor 1; 22, 23 for reactor 2; 32, 33 for reactor 3; 42, 43 for reactor 4, 52, 53 for reactor 5 and 62, 63 for reactor 6.

Gaseous phase flows from outlets at the top of the reactors for reactors 1, 2, 3 and 4. Theses outlets are identified 11 for reactor 1; 21 for reactor 2; 31, for reactor 3; 41 for reactor 4; 51 for reactor 5 and 61 for reactor 6.

Gaseous flows are introduced by lateral inlet of the reactors. The gaseous inlets for feeding reactor n with gaseous phase of reactor n+1, are identified 14 for reactor 1; 24 for reactor 2; 34 for reactor 3; 44 for reactor 4;

Steam flow is introduced by lateral inlet of reactors 5 or 6; these inlets are identified 54 for reactor 5; 64 for reactor 6.

The reactor n comprises preferably a lateral liquid inlet which is used for some of them, first, second or third, for feeding methanol. The methanol inlet is identified 17 for reactor 1, 27 for reactor 2and 37 for reactor 3.

Main raw material, that is to say, methacrylamide in an excess of sulphuric acid, coming from amidification unit 130, is fed to the first reactor 1 by inlet 9. Some water solution coming from purification unit (S8—of FIG. 1) or some fresh water is fed to the first reactor 1 by inlet identified 10. Methanol is fed mainly to the first reactor 1 via inlet 17, but some part preferably 5 to 40% of methanol can be fed to the second 2 or to the third reactor 3 by the way of valve device V10 and a control valve device VM2. Water, methanol and methacrylamide are introduced to the first reactor via control valve devices, respectively, V0, VM1, VE. Each reactor comprises a level control device LC to maintain liquid level constant, said level control device is able to activate control valve devices and by this way to regulate the liquid outlet flow. No ammoniac is introduced in any reactor or present in the reaction medium.

Low pressure preferably 3 barg to 8 barg steam is fed to the last reactor 5 (or 6) by the way of control valve device V20 and valves V8 or V9. The control valve device V20 is set by a predetermined flow FC. Molar ratio between water and methacrylamide without taking into account sulphuric acid, is between 3 and 4. It is advantageously to feed water because direct esterification of methacrylamide to MMA with methanol is not a quickly way from kinetic side. It is quicker to make hydrolysis of methacrylamide into methacrylic acid with water and then achieve esterification of methacrylic acid into methyl methacrylate with methanol. So with water introduction, esterification yield is higher. Molar ratio between steam and methacrylamide is between 1 and 2.5. So total water (liquid and steam) fed to esterification unit is between 4 to 6.5. Methanol is put in excess in comparison with methacrylamide from 1.1 to 2. Indeed the goal is to favor conversion from methacrylic acid to methyl methacrylate. Sulfuric acid mass concentration in sulphuric methacrylamide coming from amidification unit is between 55% and 70%. This number depends on amidification yield and parameters.

The counter current flow between steam and liquid is to achieve a stripping effect on each reactor. It means to extract valuable organics from spent acid. Gaseous pressure varies from 0.1 barg minimum in first reactor 1 to 1,5 barg maximum in last reactor 5 (or 6). Temperature varies from 98° C. to 102° C., preferably 98° C. to 100° C. in first reactor 1; up to from 135° C. to 145° C. maximum in last reactor 5 (or 6) and preferably from 135° C. to 138° C. for said last reactor. At the top of first reactor outlet 11, the gaseous phase flows to a partial condenser 70. The outlet temperature of partial condenser 70 is between 80 and 84° C. The goal of the devices 70 and 71, is to achieve a first separation between methacrylic acid and crude MMA. Indeed, liquid from partial condenser 70 fed a drum 71. The drum is able to separated liquid phase from gaseous phase, liquid phase being recycled to the first reactor 1. Gaseous phase flows up to a total condenser 72. The liquid "crude MMA" is recovered in a drum 74. There is a trap condenser 73 above the drum to avoid losing MMA in the vents. Crude MMA is then cooled via cooling device 80 and sent to purification section S8. Methacrylic acid concentration in crude MMA is usually less than 1 wt % in the process. By extraction MMA at the top of first reactor 1, conversion of esterification from methacrylamide to methacrylic acid and to methyl methacrylate is optimized. Indeed esterification reaction is a chemical equilibrium. In the other side, spent acid has a low organic contents downward the last reactor: between 2 wt % to 6 wt %. MMA is easily vaporized on each reactor because it forms an azeotropic mixture with methanol or with water.

Each reactor is a vertical vessel with for example torispherical heads. Heads can also be hemispherical or ellipsoidal. The vessel described has a substantially cylindrical shape, the height of the cylinder defining the vertical axis XX' of the vessel, and the diameter defining the horizontal axis YY', perpendicular the axis XX'.

Advantageously, each reactor comprises two liquid outlets, (12, 13; . . . , 62, 63) at the bottom part for spent acids outflow. These two outlets are linked to the two basket filters F and two centrifugal pumps P. At the release of the pumps, the liquid flow is partially recycled to the same reactor to ensure mixing and, remaining part of liquid is sent to the next reactor. This split is done thank to a control valve device V1 for reactor 1 and 2, V2 for reactor 2and 3, V3 for reactor 3 and 4, V4 for reactor 4 and the last esterificator working. For the last esterificator working, there is a liquid flow partially recycled to the same reactor and remaining part of liquid is sent to crystallization or treatment, thanks to control valve device V6 or V7 in the example. The purpose of basket filters F is to remove small polymers from liquid phase. Liquid line is doubled until pumps to avoid fouling, plugging or cavitation of pumps. In normal operation both pumps P are working together. A pump P is shutted-down and isolated only if a cavitation a plug is detected. Cleaning operation can be achieved for the filter or the pump without stopping all esterification section.

Figure 3:
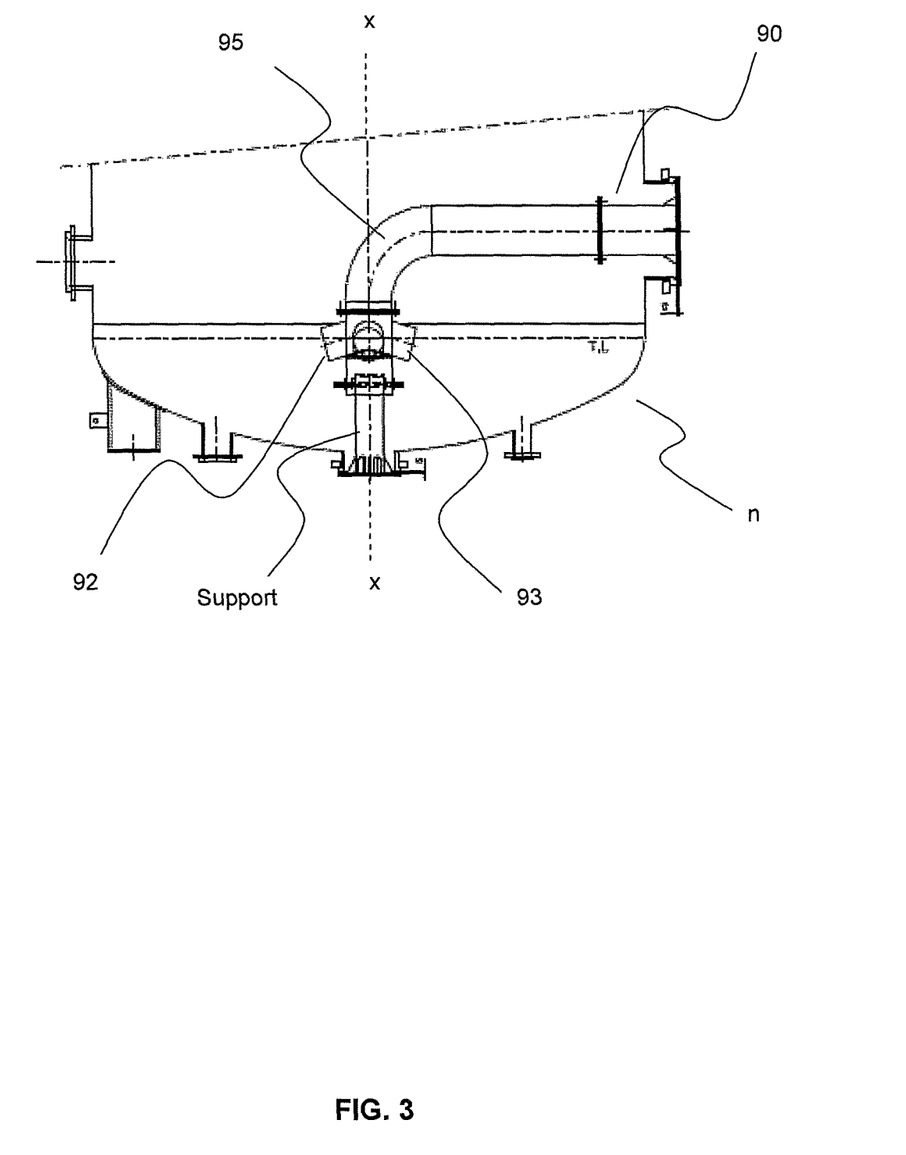
FIG. 3 represents a view of detailed cross section along a first axis XX' of a lower part of a reactor and steam distributor according to FIG. 2.

Each reactor comprises as gaseous phase distributor a steam distributor 90. The distributors 90 are located inside the lower part of each reactor 1, . . . , 6. Detailed view of steam distributor 90 is represented on FIGS. 4 and 5. The steam distributor comprises a pipe going horizontally from lateral wall of the reactor until middle of the reactor with three or four nozzles 91, . . . , 94 facing low in comparison with horizontal. Slope of nozzle is between 10° to 45° in comparison with horizontal. Lengths of nozzles are short in comparison with reactor diameter, preferably less than ½0e of the diameter. Indeed, it is preferably to avoid too much internal devices inside reactor to avoid fouling points. And as the reaction mixture is highly corrosive, nozzles are sensitive to vibration and corrosion. The steam distributors 90; ensure good mixing and stripping effect between gaseous phase and liquid phase. Due to the steam distributors 90 no mechanical agitation is needed in the esterification unit or by the esterification process according to the invention.

Figure 4:
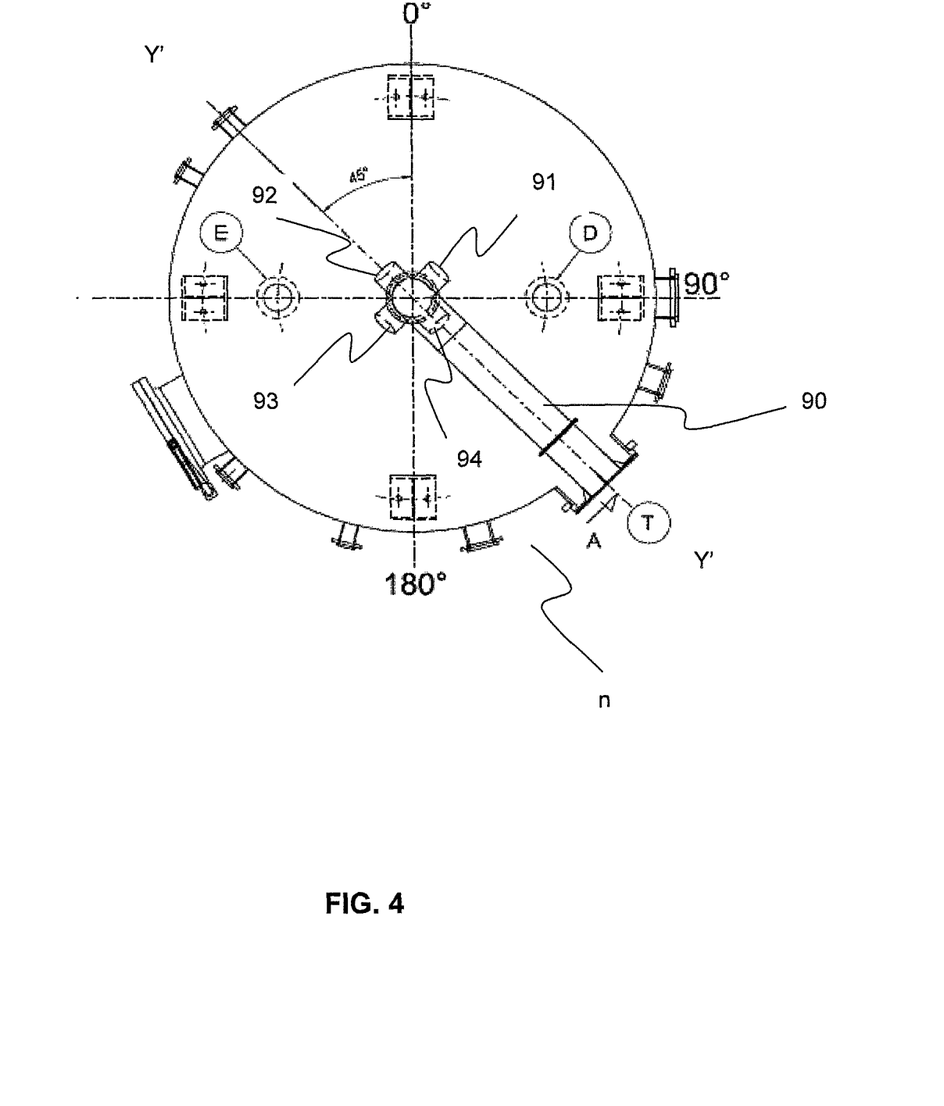
FIG. 4 represents a view of detailed cross section along a second axis YY' perpendicular the first axis XX' of the lower part of the reactor of FIG. 3.

The steam distributors introduce only steam in the reactor. No inert gas or alcohol is introduced.

Indeed, in each reactor there is a liquid phase and a gaseous phase. Liquid level L is maintained between 25% to 75% of the total height of each reactor. Gaseous phase outflow at the top of reactor from outlets. The upper part of reactor is useful to avoid dragging away liquid droplets with gaseous flow. Diameter of vessel is fixed according to maximal gas upper velocity in the reactor. Volume and height are fixed so as to ensure sufficient liquid residence time in each reactor and therefore good conversion of methacrylamide to MMA.

Preferably an anti-fouling additive and a polymerization inhibitor, represented by bloc INHIB on FIG. 2, is added to the reactors, to the partial condenser and to total condenser and trap condenser for crude MMA. More preferably the inhibitor injections are done in the 1st and 3rd reactor.

An example of available inhibitors are listed below. Moreover, it may advantageous and useful to add a demulsifier. Polymerization inhibitors are useful to prevent polymerization both during the process of preparing MMA and during storage and shipment of MMA. The polymerization inhibitor may include a water soluble or alcohol soluble polymerization inhibitor. Suitable examples include but are not limited to, hydroquinone; 4-methoxyphenol; 4-ethoxyphenol; 4-propoxyphenol; 4-butoxyphenol; 4-heptoxyphenol; hydroquinone monobenzylether; 1.2-dihydroxybenzene; 2-methoxyphenol; 2,5-dichlorhydroquinone; 2,5-di-tert-butylhydroquinone; 2-acetylhydroquinone; hydroquinone monobenzoate; 1,4-dimercaptobenzene; 1,2-dimercaptobenzene; 2,3,5-trimethylhydroquinone; 4-aminophenol; 2-aminophenol; 2-N, N-dimethylaminophenol; 2-mercaptophenol; 4-mercaptophenol; catechol; monobutylether; 4-ethylaminophenol; 2,3-dihydroxyacetophenone; pyrogallol; 1,2-dimethylether; 2-methylthiophenol; t-butyl catechol; di-tert-butylnitroxide; di-tert-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-dimethylamino 2,2,6,6-tetramethyl-piperidinyloxy; 4-amino-2,2,6,6-tetramethyl-piperidinyloxy; 4-ethanoyloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; sodium nirosophenolate; copper compounds such as copper dimethyldithiocarbamate; copper diethyldithiocarbamate; copper dibutyldithiocarbamate; copper salicylate; methylene blue; iron; phenothiazine; 1,4-benzenediamine, N-(1,4-dimethylpentyl)-N'-phenyl; 1,4-benzenediamine, N-(1,3-dimethylbutyl)-N'-phenyl; isomers thereof; mixtures of two or more thereof; or mixtures of one or more of the above with molecular oxygen. The polymerization inhibitor is typically used at levels ranging from 100 ppm to 4,000 ppm by weight.

The materials of the reactor vessels preferably include, but are not limited to, glass-lined materials. because they are cheap The last reactors (N, N+1) cannot be glass-lined material due to regular cleaning operations and fragility of this material. Other possible materials are zirconium, titanium, lead, or tantalum alloys, and nickel-based alloys such as nickel /molybdenum alloys sold as HASTELLOY B, B2, or B3, or iron/nickel alloys sold as INCOLOY. Steam distributor 90 and basket filters F are more preferably in iron/nickel alloy or in zirconium. External gaseous pipes are glass lined pipes. External liquid pipes are carbon steel pipes lined internally with polytetrafluoroethylene (PTFE), perfluoro-ethylene propylene (FEP) or perfluoroalkoxy (PFA). Pumps are lined with PFA. Partial condenser 70 and total condenser 72 are preferably graphite heat exchangers. Crude MMA drum 74 can be preferably in stainless steel AISI 316L.

According to the invention, the crude methyl methacrylate recovered from esterification unit contains mainly 50 wt % to 80 wt % of MMA, 10 wt % to 20 wt % of water and 10 wt % to 20 wt % of methanol and other (impurities). Before distillation step, most part of methanol and water is removed from methyl methacrylate by water extraction step.

The main advantage of this invention is to achieve esterification with a very good yield. It means more than 95% and advantageously more than 97%. It means for example that organic losses in spent acids are low.

The second main advantage of this invention is to achieve esterification in a reliable way. It means that there are no unplanned shut-down of esterification due to polymers fouling.

The third advantage of this invention is to produce crude MMA with rather good quality. It means that acidity and more particularly methacrylic acid content in MMA is low. And it means MMA concentration in crude MMA is rather high ie, 50 wt % to 80 wt %.

The invention claimed is:

1. An esterification unit for producing crude methyl methacrylate (MMA) from methacrylamide (MAM), and at least methanol and water, said esterification unit comprising reactors (1, . . . .n, n+1, . . . , . . . N), wherein "n" represents the number of each reactor in the series of reactors (1, 2, 3, 4, 5 etc.), and "N" represents the last reactor in the series, each reactor having an upper part and a lower part, wherein the reactors are set up in a serial way so that there is a counter current flow between a gaseous phase and a liquid phase, the liquid phase flowing from a first reactor (1) of the series to a last reactor (N), and the gaseous phase flowing from the last reactor (N) to the first reactor (1), the first reactor of the series comprising:
methacrylamide, methanol and water lateral inlets,
the last reactor (N) comprising a lateral steam inlet located at the lower part,
and each reactor (1, . . . n, n+1, . . . N) also comprising:
at least a gaseous phase outlet, at the top of the upper part,
at least a gaseous phase inlet at the lower part, the reactors being connected in such a manner that the gaseous phase outlet of reactor (n+1) is linked to the gaseous phase inlet of reactor (n), at least a liquid phase outlet located at the bottom of the lower part,
at least a lateral liquid phase inlet located at the lower part, the reactors being connected in such a manner that the liquid phase outlet of reactor (n) is linked to the lateral liquid phase inlet of reactor (n+1),
at least another lateral liquid phase inlet located at the lower part, the liquid phase outlet of reactor (n) being linked to said another lateral liquid phase inlet of said reactor (n);

said esterification unit further comprising an additional reactor (N+1) comprising:
at least a first and a second lateral liquid phase inlet located at the lower part,
at least a gaseous phase outlet at the top of the upper part,
at least a liquid phase outlet located at the bottom of the lower part, and at least a lateral steam inlet located at the lower part, said additional reactor (N+1) being connected in a parallel way to the last reactor (N) of the series in such a manner that said additional reactor (N+1) is alternatively linked to a penultimate reactor (N−1), the gaseous phase outlet of the additional reactor (N+1) being linked to a lateral gaseous phase inlet of said penultimate reactor (N−1), a liquid phase outlet of said penultimate reactor (N−1) being linked to the first lateral liquid phase inlet of the additional reactor (N+1), and the liquid phase outlet of said additional reactor (N+1) being linked to the second lateral liquid phase inlet of said additional reactor (N+1).

2. The esterification unit according to claim 1, wherein a second and/or third reactor of the series comprises a third liquid phase inlet at the lower part for feeding methanol.

3. The esterification unit according to claim 1, wherein each reactor comprises a gaseous phase distributor (90) located inside the lower part of the reactor.

4. The esterification unit according to claim 3, wherein the gaseous phase distributor (90) comprises a pipe going horizontally from a lateral wall of the reactor to the middle of the reactor, said horizontal pipe having at its end at least three nozzles.

5. The esterification unit according to claim 3, wherein a material of the gaseous phase distributors (90) is selected from an iron/nickel alloy and zirconium.

6. The esterification unit according to claim 1, wherein said unit comprises a separation means to separate methacrylic acid from crude methyl methacrylate (MMA), said separation means being connected to the gaseous phase outlet of the first reactor.

7. The esterification unit according to claim 6, wherein said separation means comprises:
- a first partial condenser for liquefying gaseous phase, having at least an inlet linked to the gaseous phase outlet of the first reactor with a temperature between 98° C. to 102° C., and at least an outlet providing liquid phase at a temperature between 80° C. and 84° C.,
- a drum device able to separate the obtained liquid phase from gaseous phase, separating acids from crude MMA, said drum device having an inlet connected to the outlet of the first partial condenser; and an acids outlet linked to the lateral liquid inlet of the first reactor and, having a gaseous phase crude MMA outlet,
- a total condenser for liquefying the gaseous phase crude MMA, said total condenser comprising a gaseous phase inlet linked to the gaseous phase crude MMA outlet of the drum device, and an outlet for a liquid phase crude MMA,
- a recovery drum linked to the outlet of the total condenser for recovering the liquid phase crude MMA, comprising a crude MMA outlet and a light components outlet,
- a trap condenser, linked to the light components outlet of the recovery drum, for recovering light components, including methanol and comprising an outlet vent,
- and a cooling device for cooling crude MMA, comprising an inlet linked to the crude MMA outlet of said recovery drum and comprising a crude MMA outlet with a concentration of MMA being of 50% to 80%.

8. The esterification unit according to claim 7, wherein the first partial condenser and the total condenser are cooled by a controlled flow of chilled water (CW).

9. The esterification unit according to claim 7, wherein the total condenser is configured to condense at least 99% of the crude MMA gaseous phase.

10. The esterification unit according to claim 1, wherein each reactor further comprises an additional liquid phase outlet, making two liquid phase outlets, a first outlet and a second outlet located at the bottom of the lower part, a first centrifugal pump being connected to said first outlet and a second centrifugal pump being connected to said second outlet, each centrifugal pump having an outlet, said outlet being linked to the lateral liquid phase inlets located at the lower part of two successive reactors.

11. The esterification unit according to claim 10, wherein, said first outlet and said second outlet are each respectively connected to said first centrifugal pump and said second centrifugal pump via a basket filter (F).

12. The esterification unit according to claim 11, wherein a material of the basket filters (F) is selected form an iron/nickel alloy and zirconium.

13. The esterification unit according to claim 1, wherein each reactor comprises at least a temperature control device (TA), a pressure control device (PA) and level control device (LC), and said level control device regulates the flow of liquid though the liquid phase outlet to maintain a constant liquid level inside each reactor.

14. The esterification unit according to claim 13, wherein the lateral liquid phase flow is fed to reactors (n) and (n+1), via control valve devices activated by the level control device (LC).

15. The esterification unit according to claim 1, wherein said unit comprises a steam control flow device (V20, FC) able to regulate the steam flow according a predetermined flow rate (FC).

16. The esterification unit according to claim 1, wherein, said unit comprises 3 to 8 reactors (1, . . . n, n+1, . . . N), being set up in serial way and the additional reactor (N+1) being connected in a parallel way to the last reactor (N).

17. The esterification unit according to claim 16, wherein said unit has 5 or 6 total reactors, wherein a material of the last reactors (N, N+1) is selected from zirconium, titanium, lead, nickel/molybdenum alloys, iron/nickel alloys, and tantalum alloys; and a material of the remaining reactors is selected from glass-lined materials.

18. The esterification unit according to claim 1, wherein the unit comprises external pipes for transporting the gaseous phase, and said external pipes are glass lined pipes.

* * * * *